United States Patent [19]

Gersberg

[11] Patent Number: 5,195,892
[45] Date of Patent: Mar. 23, 1993

[54] BONE-INTEGRATED DENTAL IMPLANT SYSTEM

[75] Inventor: Juan J. Gersberg, Buenos Aires, Argentina

[73] Assignee: Odontit S.A., Buenos Aires, Argentina

[21] Appl. No.: 733,752

[22] Filed: Jul. 23, 1991

[30] Foreign Application Priority Data

Jul. 23, 1990 [FR] France ................ 90 09393

[51] Int. Cl.$^5$ .............................................. A61C 8/00
[52] U.S. Cl. .................................... 433/174; 433/173
[58] Field of Search ................... 433/173, 174, 175

[56] References Cited

U.S. PATENT DOCUMENTS

| | | | |
|---|---|---|---|
| 3,589,011 | 6/1971 | Sneer | 433/174 |
| 4,780,080 | 10/1988 | Haris | 433/173 |
| 4,850,870 | 7/1989 | Lazzara et al. | 433/173 |
| 4,854,872 | 8/1989 | Detsch | 433/173 |
| 4,995,810 | 2/1991 | Soderberg | 433/174 |
| 5,061,181 | 10/1991 | Niznick | 433/174 |

FOREIGN PATENT DOCUMENTS

| | | |
|---|---|---|
| 0320791 | 6/1989 | European Pat. Off. . |
| 8905499 | 10/1989 | Fed. Rep. of Germany . |
| 2571607 | 4/1986 | France . |
| 87/00742 | 5/1988 | PCT Int'l Appl. . |
| 2199626 | 7/1988 | United Kingdom . |

*Primary Examiner*—John J. Wilson
*Attorney, Agent, or Firm*—Darby & Darby

[57] ABSTRACT

An integrated dental implant system includes a cylindrical implant and a prosthetic supporting structure for supporting a dental prosthesis. The support structure is fixedly securable to the implant. The implant system further includes two transfer keys for putting the implant and a cover screw acting as a healing cap in place. The system also includes a transfer cap and an analog of the prosthetic support for producing a model of the prosthesis in a laboratory.

7 Claims, 2 Drawing Sheets

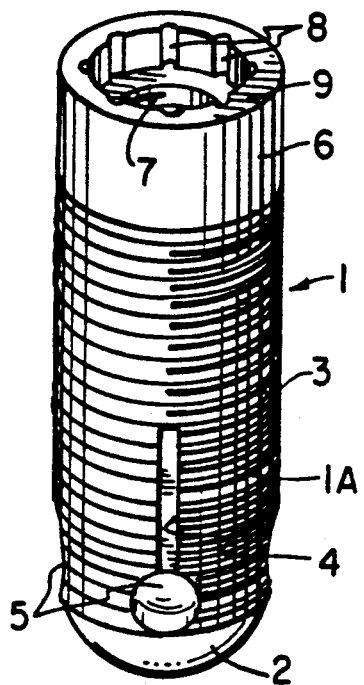
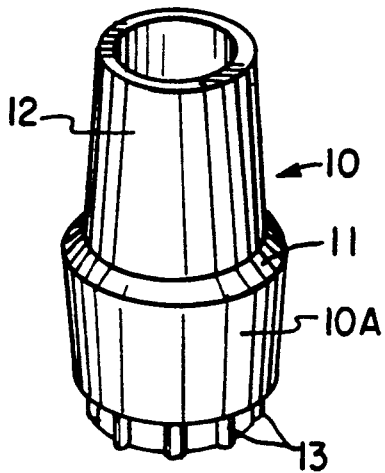
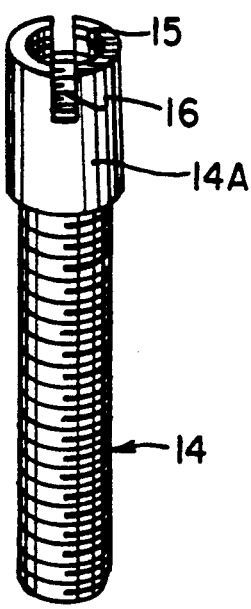
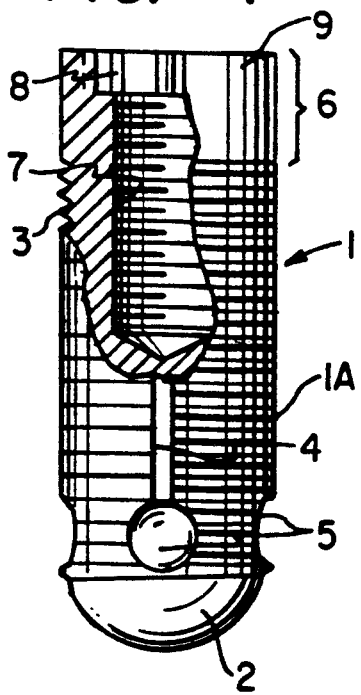
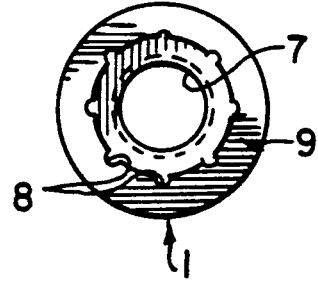
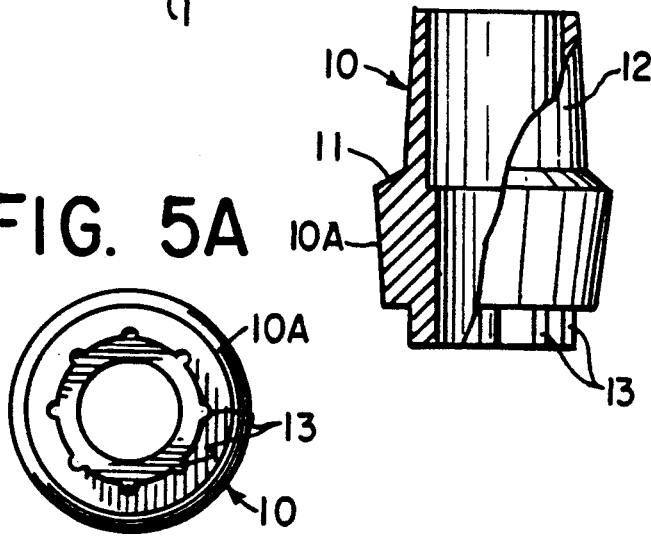
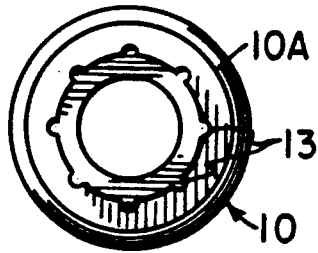

5,195,892

BONE-INTEGRATED DENTAL IMPLANT SYSTEM

BACKGROUND OF THE INVENTION

The present invention relates to a dental implant system and, in particular, to a bone-integrated dental implant system including an implant to be anchored in a jawbone and a prosthetic supporting structure securable to the implant.

Bone-integrated dental implant systems including an implant anchor and a prosthetic support securable thereto are known. The present invention provides a bone-integrated dental implant system that can be reliably and easily secured in the jawbone.

SUMMARY OF THE INVENTION

The system according to the invention comprises an implant securable in the jawbone, a prosthetic support, and a fixation screw for securing the prosthetic support to the implant. The implant of the invention has a cylindrical body with an external thread over the lower portion and an upper smooth neck portion. At its lower end, the cylindrical body ends with a hemispherical dome. A plurality of slots are provided at the lower portion of the threaded part of the body. At the upper, smooth neck end, the implant has a cylindrical cavity with a striated portion for receiving the prosthetic support structure. The prosthetic support structure also has a striated end portion cooperating with the striated portion of the cylindrical cavity for securing the prosthetic support structure to the implant. Above the striated portion, the support structure has a gingival portion that extends through the patient's gum.

The implant system further includes a transfer key for putting the implant in place, a cover screw to cover the end of the implant before the support is affixed and a transfer key for putting the cover screw in place. The system also includes a transfer cap and an analogue of the prosthetic support structure for producing a model in a laboratory.

BRIEF DESCRIPTION OF THE DRAWINGS

The above-mentioned and other features of the present invention and the manner of attaining them will become more apparent, and the invention itself will be best understood, from the following detailed description of the preferred embodiment of the invention when read in conjunction with the accompanying drawings, wherein:

FIG. 1 shows a perspective view of an implant according to the present invention;

FIG. 2 shows a perspective view of a prosthetic support structure according to the present invention;

FIG. 3 shows a perspective view of a fixation screw used for connecting the prosthetic support structure to the implant;

FIG. 4 shows a partial cross-sectional elevation view of the implant shown in FIG. 1;

FIG. 4A shows a top view of the implant shown in FIG. 4;

FIG. 5 shows a partial cross-sectional elevational view of the prosthetic support structure shown in FIG. 2;

FIG. 5A shows a bottom view of the support structure shown in FIG. 5;

DESCRIPTION OF THE PREFERRED EMBODIMENT

Figure 6:
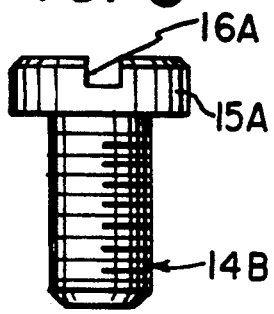
FIG. 6 shows a perspective view of a prosthetic screw.

An implant according to the present invention is shown in FIG. 1. It has an elongated cylindrical body 1A and a hemispherical dome portion at the lower end of the cylindrical body. The cylindrical body has an external thread 3 along almost the entire length thereof, but it has a smooth neck portion 6 at its upper end. In its lower portion, the threaded part of the cylindrical body has a plurality of vertical grooves 4 (three in the preferred embodiment) the purpose of which is to facilitate securing of the implant in the maxillae or jawbone of the patient. In its end portion adjacent to the hemispherical dome 2, the body 1A has four diametrically opposite cylindrical depressions or vents 5 for promoting securing the implant in the bone when new bone grows into those vents. The depressions 5 have a depth of about 0.2 mm.

The smooth neck portion is provided so that the thread will not be visible when the implant is installed, and it insures better hygiene to guard against bacterial invasion of the site.

The cylindrical body 1A has an internal threaded bore 7 and a cylindrical cavity at its upper end for receiving the prosthetic superstructure. The internal thread extends up to the middle of the implant in the present embodiment. The cylindrical cavity has striations 8 for preventing rotation of the prosthetic superstructure. The upper end surface 9 of the implant is smooth. The diameter and the length of the implant may be varied in accordance with individual cases, i.e., according to the structure of the patient's jawbone and gum at the site.

The prosthetic superstructure includes a prosthetic support structure 10 and a fixation screw 14. The prosthetic support structure 10 has a truncated cone-shaped gingival portion 10A connected by a shoulder 11 to a further cone-shaped portion 12. At the bottom of the gingival portion 10A, there is provided a striated projecting portion 13 that cooperates with the striated cavity portion 8 of the implant 1 to prevent rotation of the support structure relative to the implant. The length of the gingival portion 10A may be varied in accordance with the gingival thickness of the patient. The shoulder 11 may be positioned at a predetermined height either above or below the gum. The upper cone 12 also may have different lengths and cone angles. The dental prosthesis is mounted on the cone 12 abutting the shoulder 11.

The prosthetic support structure 10 is secured to the implant 1 with the fixation screw 14 which extends therethrough. The head 14A of the screw 14 has an internal threaded opening 15 to which the dental prothesis is secured with a prosthetic screw 14B (FIG. 6) once the prosthetic device is placed over the upper cone 12. The head 14A of the screw 14 also has a slot 16 that facilitates its screwing into the implant 1.

The prosthetic screw 14B (FIG. 6) is also provided with a head 15A having a slot 16A for a screwdriver.

Figure 7:
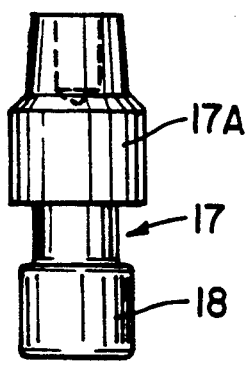
FIG. 7 shows an elevational view of an analogue of the prosthetic support structure used for manufacturing the prosthesis in a laboratory.

An analogue 17 of the support structure 10 has a model of a maxillae mounted on it for manufacture of the dental prosthesis in a laboratory. This analogue 17 is shown in FIG. 7. Its upper portion 17A presents a duplicate of the support structure 10 shown in FIG. 2. The lower portion 18 of the analogue 17 is designed for mounting the analogue 17 on the plaster model.

Figure 8:
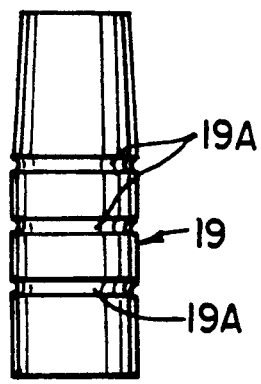
FIG. 8 shows an elevational view of a transfer cap used for taking impressions to form crowns or bridges.

A transfer cap 19 shown in FIG. 8 is made of a calcinable material and used for taking impressions, as well as for forming crowns or bridges through which the prosthetic screw 14B would extend. The slots 19A in cap 19 are provided to facilitate its withdrawal during the taking of impressions. The cap 19 is seated on the shoulder 11 of the support structure. The analogue 17 is mounted over the cap 19 on the shoulder 11 of the support structure with a clearance which insures a proper finish of the prosthesis with porcelain or acrylic.

Figure 9:
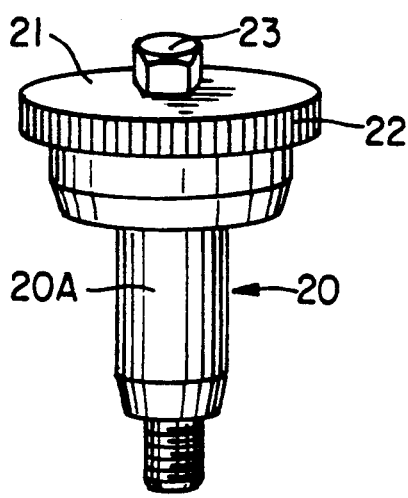
FIG. 9 shows a perspective view of a transfer key for positioning the implant in place.

The implant is put in place in the maxilla of a patient with aid of a transfer key 20 shown in FIG. 9, which also serves for its packing. The transfer key has a cylindrical body 20A fixed to a plastic pad 21 having striations 22. A screw 23 extending through the transfer key 20 is used for fixing the implant beneath the cylindrical body 20A. By engaging the striations 22 manually, the dental surgeon may twist the key 20 so the implant attached to it is threaded into an opening prepared in the patient's maxilla.

Figure 10:
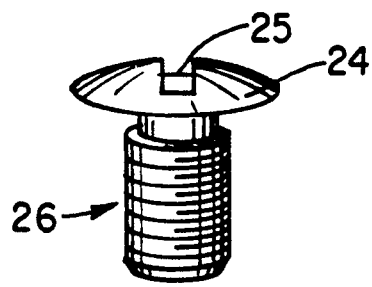
FIG. 10 shows a perspective view of a cover screw for the implant.
Figure 11:
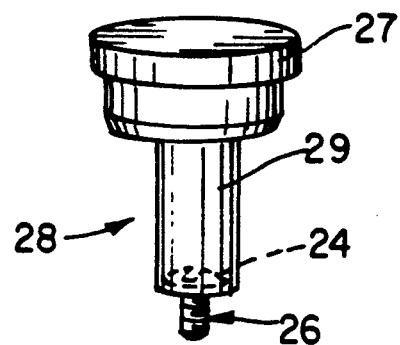
FIG. 11 shows a perspective view of a transfer key for placing the cover screw in place.

The cover screw 26 shown in FIG. 10 is secured to the implant 1 by engagement with the internal threaded bore 7 of the later. The cover screw 26 has a spherical head 24 with a slot 25. The cover screw 26 is put in place with aid of a transfer key 28 shown in FIG. 11. The transfer key 28 has a plastic pad 27 and a cylindrical peg 29 which is hollow. The cover screw 26 is fixed therein by simply applying pressure thereto. If the implant is to be kept out of operation until it is firmly anchored in place by growth of new bone, especially into the vent, the cover screw 26 may be installed first. When healing occurs it is removed and then the support structure 10 is fixed to the implant.

While various details of the invention have been shown, it will be clear to those skilled in the art that changes may be made therein which still fall within the spirit and scope of the invention.

What is claimed is:

1. A bone-integrated dental implant system for supporting a dental prosthesis installed in the jawbone of a patient, comprising:

an implant including a cylindrical body having an externally threaded portion and a hemispherical dome at one end of the cylindrical body, the threaded portion having a plurality of vertically extending grooves extending through the threaded portion but stopping short of the threads toward the other end of the cylindrical body and at least one pair of diametrically opposite depressions for securing the implant in the jawbone, the cylindrical body further having a smooth neck portion at the other end that extends to the threaded portion, a threaded internal bore at the other end with a first diameter, and a cylindrical cavity at the other end abutting said threaded internal bore and having a second diameter larger than the first diameter; and a dental prosthesis supporting superstructure securable in the cylindrical cavity and including screw means for connecting it with the implant.

2. A bone integrated dental implant system as set forth in claim 1 wherein the prosthetic supporting superstructure has a gingival truncated cone-shaped portion, the system further comprising means for preventing rotation of the prosthetic supporting superstructure relative to the implant, the rotation preventing means comprising an internal striation in the cylindrical cavity and an externally striated portion projecting from a bottom of the gingival portion of the supporting superstructure.

3. A bone integrated dental implant system as set forth in claim 1 wherein the internal bore has an inner thread, the screw means comprises a fixation screw having a cylindrical threaded portion engageable with the inner thread and a hollow head with an internal thread and a slot.

4. A bone integrated dental implant system as set forth in claim 3 further comprising a cover screw for the implant having a threaded portion receivable in the threaded bore of the implant and a hemispherical head adapted to cover the cylindrical cavity.

5. A bone integrated dental implant system as set forth in claim 3 further comprising a transfer cap for making an impression of the implant and having a cylindrical projection with a plurality of circumferential grooves, the prosthetic supporting superstructure having a shoulder for receiving the transfer cap thereon.

6. A bone integrated dental implant system as set forth in claim 3 further comprising an implant transfer key for putting the implant in place, said implant transfer key having a striated pad, a cylindrical body projecting from the pad, and a screw extending therethrough for securing the implant transfer key to the implant.

7. A bone integrated dental implant system as set forth in claim 3 further comprising a cover transfer key for putting in place a cover screw, said cover transfer key having a plastic pad and a hollow cylindrical projection extending from the pad for receiving the cover screw therein.

* * * * *